(12) United States Patent
Velamuri et al.

(10) Patent No.: US 11,705,246 B2
(45) Date of Patent: *Jul. 18, 2023

(54) SYSTEM, APPARATUS, METHOD, AND GRAPHICAL USER INTERFACE FOR SCREENING

(71) Applicants: Narasimheswara Sarma Velamuri, Houston, TX (US); Marcus Joel Christian Persson Rydberg, Houston, TX (US)

(72) Inventors: Narasimheswara Sarma Velamuri, Houston, TX (US); Marcus Joel Christian Persson Rydberg, Houston, TX (US)

( * ) Notice: Subject to any disclaimer, the term of this patent is extended or adjusted under 35 U.S.C. 154(b) by 603 days.

This patent is subject to a terminal disclaimer.

(21) Appl. No.: 16/773,804

(22) Filed: Jan. 27, 2020

(65) Prior Publication Data
US 2020/0234828 A1    Jul. 23, 2020

Related U.S. Application Data

(62) Division of application No. 14/998,182, filed on Dec. 24, 2015, now Pat. No. 10,592,637.

(60) Provisional application No. 62/116,701, filed on Feb. 16, 2015, provisional application No. 62/096,754, filed on Dec. 24, 2014.

(51) Int. Cl.
G16H 50/20    (2018.01)
G16H 50/30    (2018.01)
G16H 40/67    (2018.01)

(52) U.S. Cl.
CPC ............. *G16H 50/20* (2018.01); *G16H 40/67* (2018.01); *G16H 50/30* (2018.01)

(58) Field of Classification Search
CPC ......... G16H 50/20; G16H 40/67; G16H 50/30
See application file for complete search history.

(56) References Cited

U.S. PATENT DOCUMENTS

| | | |
|---|---|---|
| 2005/0130185 A1 | 6/2005 | Lu et al. |
| 2006/0173663 A1 | 8/2006 | Langheier et al. |
| 2006/0246495 A1 | 11/2006 | Garrett et al. |
| 2011/0137852 A1 | 6/2011 | Gajic et al. |
| 2014/0037649 A1 | 2/2014 | Brandon et al. |
| 2014/0249850 A1 | 9/2014 | Woodson et al. |
| 2014/0322207 A1 | 10/2014 | Johansson et al. |
| 2015/0238692 A1 | 8/2015 | Peterson et al. |
| 2016/0168638 A1 | 6/2016 | Garrett et al. |

OTHER PUBLICATIONS

International Preliminary Report on Patentability issued in PCT Application No. PCT/US15/00419, dated Aug. 25, 2017. [12 pages].
International Search Report dated May 17, 2016, during the prosecution of International Application No. PCT/US2015/000419. [3 pages].
Written Opinion dated May 17, 2016, during the prosecution of International Application No. PCT/US2015/000419. [11 pages].

*Primary Examiner* — Jerry Lin
(74) *Attorney, Agent, or Firm* — Alberto Q. Amatong, Jr.; Amatong McCoy LLC

(57) ABSTRACT

Disclosed is a computer-implemented method of screening a patient for end organ damage due to infection. The method entails receiving patient data relating to an identified patient in a computing system including a processor and memory coupled to the processor, wherein the memory stores programmable instructions executable by the processor. The presence of Systemic Inflammatory Response Syndrome is determined and then the presence or absence of a high probability of end organ damage due to infection. Each of the determining steps includes receiving, on a graphical user interface, one or more user selections presented on the graphical user interface and executing programmable instructions based on received user selections.

28 Claims, 10 Drawing Sheets

SIRS SCREENING (330)

TEMPERATURE
- < 96.8 °F ☐
- > 100.1 °F ☐
- NORMAL ☑

HEART RATE
- < 60 BPM ☑
- > 100 BPM ☐
- NORMAL ☐

CONDITIONS
- RESPIRATORY RATE > 20 BPM ☐
- TOXIC APPEARANCE ☑
- ALTERED MENTAL STATE ☐
- WBC > 12K OR 4k; BANDS > 10% ☑
- BG < μGDL-1 ☐

PATIENT IS SIRS POSITIVE

SIRS +
CLICK HERE TO PROCEED WITH FURTHER SCREENING

SIRS SCREENING (320)

TEMPERATURE
- < 96.8 °F ☐
- > 100.1 °F ☑
- NORMAL ☐

HEART RATE
- < 60 BPM ☑
- > 100 BPM ☐
- NORMAL ☐

CONDITIONS
- RESPIRATORY RATE > 20 BPM ☐
- TOXIC APPEARANCE ☐
- ALTERED MENTAL STATE ☐
- WBC > 12K OR 4k; BANDS > 10% ☐
- BG < μGDL-1 ☐

PATIENT IS SIRS POSITIVE

SIRS+
CLICK HERE TO PROCEED WITH FURTHER SCREENING

FIG. 3B

SIRS + SCREENING

VARIANCE PROBABILITY BIOMARKER STAGE

- SUSPECTED INFECTION ☐
- RECENT ANTIBIOTIC USE ☐
- RECENT PROCEDURE ☐
- NONE OF THE ABOVE ☐

MODIFYING FACTORS

- CIRRHOSIS / ESLD ☐
- ESRD ☐

FIG. 4A

SIRS + SCREENING

VARIANCE PROBABILITY BIOMARKER STAGE

- SUSPECTED INFECTION ☐
- RECENT ANTIBIOTIC USE ☐
- RECENT PROCEDURE ☐
- NONE OF THE ABOVE ☑

MODIFYING FACTORS

- CIRRHOSIS / ESLD ☐
- ESRD ☐

SEVERE SEPSIS NEGATIVE

EXIT
CLICK HERE TO EXIT

FIG. 4B

SEVERE SEPSIS SCREENING

510

CONDITIONS

- ☐ BP < 90 / 60 mmHg
- ☐ MAP < 65 mmHg
- ☐ O2 SAT < 92%
- ☐ VENOUS / ART LACTATE
- ☐ DIC / PETECHIAE
- ☐ PLT COUNT < 100,000
- ☐ MECHANICAL VENTILATION
- ☐ DECREASED URINE OUT PUT
- ☐ NONE OF THE ABOVE

FIG. 5A

SIRS + SCREENING

430

VARIANCE PROBABILITY BIOMARKER STAGE

- ☐ SUSPECTED INFECTION
- ☑ RECENT ANTIBIOTIC USE
- ☑ RECENT PROCEDURE
- ☐ NONE OF THE ABOVE

MODIFYING FACTORS

- ☐ CIRRHOSIS / ESLD
- ☐ ESRD

SEVERE SEPSIS IS PROBABLE

SEPSIS
CLICK HERE TO PROCEED
WITH FURTHER SCREENING

FIG. 4C

SEVERE SEPSIS SCREENING — 530

CONDITIONS
- BP < 90 / 60 mmHg ☐
- MAP < 65 mmHg ☐
- O2 SAT < 92% ☐
- VENOUS / ART LACTATE ☐
- DIC / PETECHIAE ☐
- PLT COUNT < 100,000 ☐
- MECHANICAL VENTILATION ☐
- DECREASED URINE OUT PUT ☑
- NONE OF THE ABOVE ☐

SEVERE SEPSIS POSITIVE

ALERT
CLICK HERE TO ALERT M.D.
ADMINISTRATOR / PHARMACY

FIG. 5C

SEVERE SEPSIS SCREENING — 520

CONDITIONS
- BP < 90 / 60 mmHg ☐
- MAP < 65 mmHg ☐
- O2 SAT < 92% ☐
- VENOUS / ART LACTATE ☐
- DIC / PETECHIAE ☐
- PLT COUNT < 100,000 ☐
- MECHANICAL VENTILATION ☐
- DECREASED URINE OUT PUT ☐
- NONE OF THE ABOVE ☑

SEVERE SEPSIS NEGATIVE

EXIT
CLICK HERE TO EXIT

FIG. 5B

SYSTEM, APPARATUS, METHOD, AND GRAPHICAL USER INTERFACE FOR SCREENING

The present application is a Divisional application of U.S. application Ser. No. 14/998,182 filed on Dec. 24, 2015 (now allowed), which claims the benefit of U.S. Provisional Application No. 62/096,754 filed on Dec. 24, 2014, and U.S. Provisional Application No. 62/116,701 filed on Feb. 16, 2015. Each of these disclosures is hereby incorporated by reference for all purposes and made a part of the present disclosure.

BACKGROUND

The present disclosure relates generally to a system, apparatus, method, and graphical user interface for screening, diagnosing, managing and\or treating a patient with a medical condition. In particular, the present disclosure is directed to screening or diagnosing a medical condition, and even more particularly, in respect to end organ damage due to infection. The present disclosure also relates to a computer-implemented method of screening a patient.

Potentially life-threatening complications can arise from an immune response triggered by infection. Patients can develop a severe response to an infection from almost any medical condition including: surgery, minor medical or dental procedures, postpartum (i.e., complications from childbirth), trauma, animal bites, or infections acquired inside or outside the hospital. Chemicals released by the body to fight the infection trigger inflammatory responses. As sepsis progresses to septic shock, blood pressure drops dramatically, which may result in damage to multiple organ systems and even death. According to the CDC's National Center for Health Statistics, the number of people seen in U.S. hospitals in 2008 increased from about 621,000 in 2008 to over 1.1 million. See e.g., cdc.gov/sepsis/datareports. The number of cases has been rising each year.

Treatment of sepsis currently focuses on early recognition of the condition to minimize end-organ damage and dissemination of the infection. The hallmarks of sepsis are easily recognized at the bedside but initial evidence of sepsis are frequently missed by health care providers who are not looking for it. Also, due to the labor demands of today's health care enterprise, health care providers are simply unavailable to monitor important changes in patient status. By today's standard of care, timely treatment depends on the ability to diagnose sepsis early and entails the following: (i) intervention in the first three hours, including obtaining blood cultures to detect infection in the blood; (ii) early administration of broad-spectrum antibiotics; (iii) measurement of venous lactate as a marker of tissue hypoperfusion (a medical condition in which an organ or extremity doesn't have enough blood); and (iv) administration of intravenous crystalloids (fluids that contain electrolytes). Depending on information derived from the clinical situation, treatment may further entail: (i) initiation of central venous access (placement of an intravenous catheter in the patient's neck or groin to access large bore veins); (ii) measurement of arterial blood pressure by placement of a catheter in a patient's artery; and (iii) initiation of vasopressor medications (medications that raise blood pressure by causing very strong constriction of arteries).

BRIEF SUMMARY

Disclosed herein are a system, method, apparatus, and graphical user interface for screening, managing, diagnosing and\or treating a patient with a medical condition. Also disclosed are such a system, method, apparatus, and graphical user interface for screening a patient for end organ damage due to infection. The system, method, apparatus, and graphical user interface are equally and more suitable for screening for sepsis, given that the associated complications and treatment are much the same. Disclosures described herein in relation to sepsis are typically applicable to end organ damage due to infection (and vice-versa). The method is preferably a computer-implemented method and the system preferably includes a handheld or locally stationed device connected with one or more processor(s), a memory storing programmable instructions, and input/output user interface.

In one aspect, a computer-implemented method of screening a patient for end organ damage due to infection is described. The method includes receiving patient data in a computing system including a processor and memory coupled to the processor, wherein the memory stores instructions executable by the processor. Such a computing system may be composed of a single hand-held computing device or an entire local or cloud-based network, or equal, and variations thereof and in between. The presence of Systemic Inflammatory Response Syndrome (SIRS) is determined and then, the presence or absence of a high probability of end organ damage due to infection is determined. Each of the determining procedure or step is performed by receiving, on or via a graphical user interface, one or more affirmative user selections presented on the graphical user interface. Preferably, the determining procedure or step includes executing instructions stored in memory, with said user selections as input, to determine patient status relating to the presence of Systemic Inflammatory Response Syndrome or the presence of a high probability of end organ damage due to infection. As described herein, software may be packaged in an Application, including computer programs with algorithms for determining or screening, as described above, with user or system supplied patient data as input.

In another aspect, a method of screening a patient for end organ damage due to infection is described. The method entails providing patient data relating to an identified patient into a computing system including a processor and memory coupled to the processor, wherein the memory stores programmable instructions executable by the processor, determining the presence of Systemic Inflammatory Response Syndrome, and determining the presence or absence of a high probability of end organ damage due to infection. Each of the preceding determining steps includes inputting, on a graphical user interface, one or more user selections presented on the graphical user interface and initiating execution of programmable instructions based on the inputted user selections.

In another aspect, a computing system is also described having at least one processor, at least one display, and memory coupled to the at least one processor. The memory stores programmable instructions executable by the processor to present a plurality of graphical user interfaces on the display, including a first graphical user interface and a second graphical user interface, and programmable instructions executable to determine the presence of a medical condition based on user selected patient information received on the graphical user interfaces. The first user interface presents, as user selection options, patient related observations or conditions (e.g., physical measurements), such that executing instructions includes comparing user selected patient related conditions received on the user interface with a screening criteria to indicate the presence of Systemic Inflammatory Response Syndrome. The second user interface presents, as user selection options, a plurality of clinical judgment-based parameters, such that executing instructions includes comparing user selected clinical judgment-based parameters received on the user interface with a screening criteria to indicate a high probability of end organ damage due to infection. The programmable instructions are further executable to generate the second user interface upon the indication of the presence of Systemic Inflammatory Response Syndrome. As further described herein, the user selections may be provided or prompted on graphical user interfaces of a hand-held computing device, such as tablet, and the user merely activates the prompt to make the selection. Execution of the programmable instructions (i.e., screening algorithm) may be initiated by activating a second, subsequent prompt.

BRIEF DESCRIPTION OF THE DRAWINGS

A more complete and thorough understanding of the present embodiments and advantages thereof may be acquired by referring to the following description taken in conjunction with the accompanying drawings:

FIGS. 2B and 2C are simplified schematics of an alternative exemplary system for or through which one or more step of the method of FIGS. 1 and 1A-1E may be performed, in accordance with an embodiment of the present disclosure;

FIGS. 3A-3C are representative graphical user interfaces for use with the system and method of FIG. 1, according to one embodiment of the present disclosure;

FIGS. 4A-4C are representative graphical user interfaces for use with the system and method of FIGS. 1 and 1A-1E, according to one embodiment of the present disclosure;

FIGS. 5A-5D are representative graphical user interfaces for use with, or which may be generated by, the system and method of FIGS. 1 and 1A-1E, according to one embodiment of the present disclosure.

DETAILED DESCRIPTION

Before any embodiments are explained in detail, it is to be understood that the systems, apparatus, methods, user interfaces, and products according to the present disclosure are not limited in its application to the details in the examples provided in this Detailed Description. Specific examples pertaining to the management and diagnosis of a patient, potentially with end organ damage due to infection or sepsis, are provided for illustration only. The arrangement of steps in the process or the components in the system described in respect to a patient with end organ damage due to infection or sepsis (potentially) may be varied in further embodiments in response to different conditions, objectives, and requirements. In such further embodiments, steps may be carried out in a manner involving different environmental conditions, analyses thereof, and responses thereto, as well as to different collections of data. Moreover, the description that follows includes exemplary apparatuses, methods, techniques, and instruction sequences that embody techniques of the disclosed subject matter. It is understood, however, that the described embodiments may be practiced without these specific details or employing only portions thereof.

As used herein, the terms "managing" or "screening" as directed to a patient or subject suspected of having a medical condition of interest may encompass one or more of screening, diagnosing, treating, and observing the patient or subject and collecting data therefrom. Moreover, the terms managing or screening encompasses such interaction with a patient or subject that does not result in or confirm the presence of the object medical condition (i.e., sepsis), as well as such interaction that does.

Notwithstanding the above, the present Detail Description relies on a generally computer-implemented and\or software-implemented process of screening a patient for end organ damage due to infection or sepsis to illustrate relevant concepts. The described process(es) also provides the preferred modes of carrying out the concepts in commercial applications. The present disclosure is, of course, not limited to screening, diagnosing, and managing for end organ damage due to infection or sepsis, as the concepts and embodiments provides a generalized platform for screening, diagnosing, and managing other medical conditions. Moreover, certain aspects of the described systems or processes, including certain graphical user interfaces and the use thereof, may be applicable to or in other patient care practices.

Figure 1A:
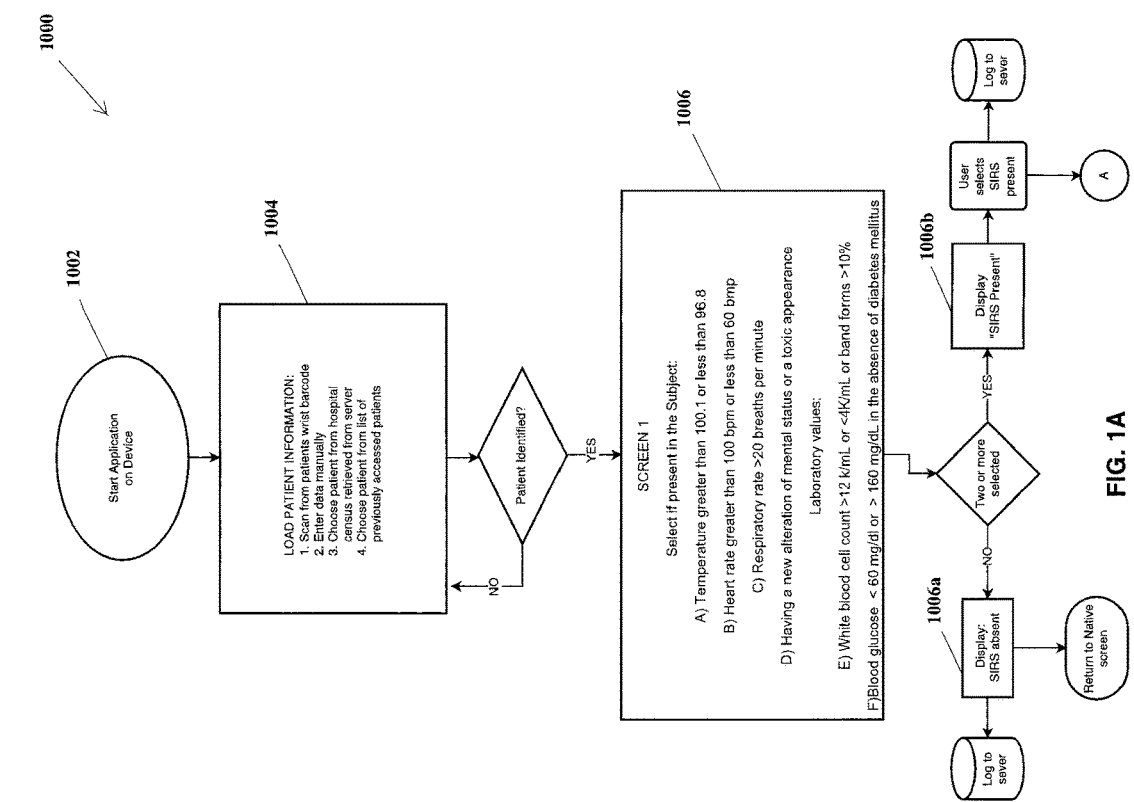
FIGS. 1A-1E is a flowchart illustrating a preferred method of screening, according to the present disclosure.
Figure 1:
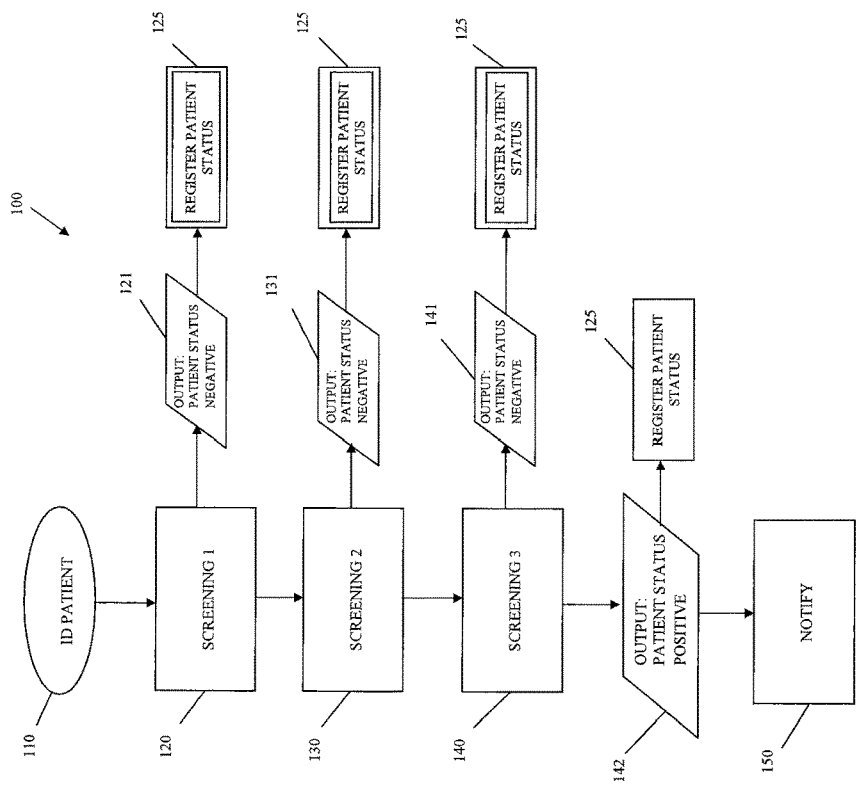
FIG. 1 is a simplified block diagram illustrating a method of screening according to the present disclosure.

The simplified flowchart 100 of FIG. 1 presents, in basic terms, an exemplary method of screening for a medical condition, according to the present disclosure. The flowchart 1000 in FIGS. 1A-1E provides a more detailed description of an exemplary process or method of screening for a patient for sepsis that is particularly suited for implementation by a health care provider-user in a hospital or other health care environment wherein a patient is present (wherein like reference numerals are used to indicate like elements). The method according to either FIG. 1 or FIGS. 1A-1E is preferably and, more suitably, implemented utilizing a mobile or hand-held computing device storing executable programmable instructions and communicating with an electronic network (as discussed below in respect to FIGS. 2A-2C). The programmable instructions are executable to generate and operate graphical user interfaces and to run screening algorithms for determining and/or outputting patient status in respect to the presence or probability of end organ damage due to infection or sepsis (or other medical condition). Such programmable instructions may be initiated by a health care provider-user entrusted with the computing device and preferably, at bedside.

Figure 5D:
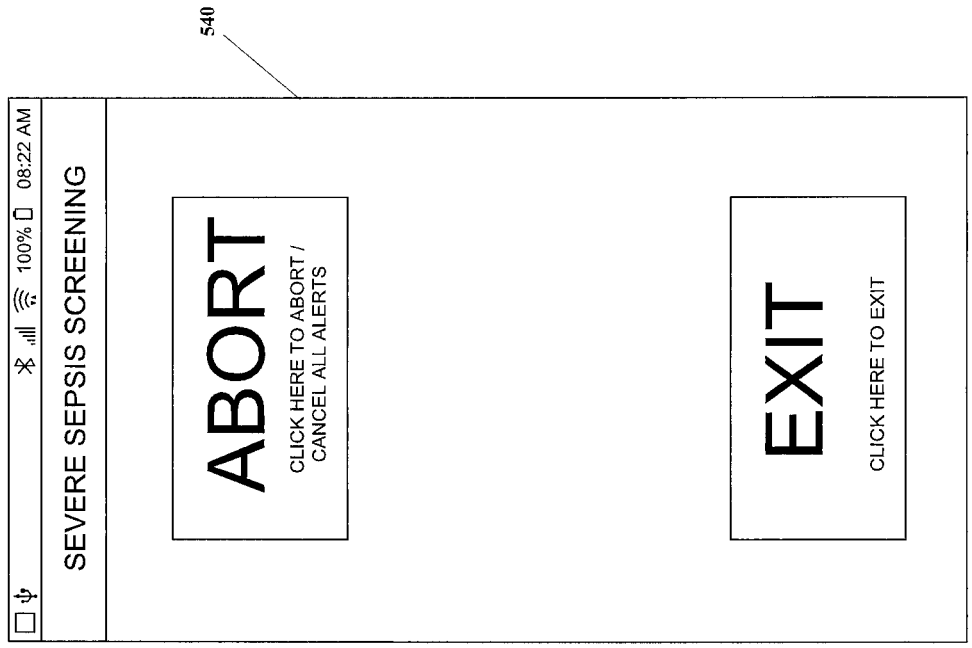

Referencing FIG. 1, the method is particularly suited for screening a patient for the potential for end-organ damage due to infection. In one aspect, the method is divided into three screening process stages 120,130,140 each of which may output one of two results (i.e., negative or positive), thereby advancing or diverting and ceasing the screening process. In another aspect, each of the three screening stages 120, 130, 140 is facilitated by availability of a hand-held computing device (storing executable programmable instructions) and a graphical user interface displayed thereon. Exemplary graphical user interfaces according to the disclosure are illustrated in FIGS. 3-5. Accordingly, the screening process stages 120, 130, 140 may be performed by a health care provider-user, at bedside, through operation of the computing device and the inputting of patient-related information via the graphical user interface.

The process is commenced by identifying the patient 110, which preferably includes identifying and\or loading known patient information. Further, the patient may be registered on a system or network (see e.g., FIGS. 2A-2C), and identified on an electronic dashboard (see e.g. FIG. 6 and accompanying description below). In the first stage 120, patient information selected or collected provides input into an algorithm for determining the presence of Systemic Inflammatory Response Syndrome. The algorithm is run by initiating execution of the appropriate instructions via the graphical user interface. If a negative determination is made, the process outputs a patient status indicating the absence of Systemic Inflammatory Response Syndrome (121). As discussed below in more detail (see FIG. 2) in respect to Systemic Inflammatory Response Syndrome, a positive patient status is determined upon the detection and\or selection of two of a set of criteria. Among other things, the algorithm compares the user selections received on the graphical user interface with a screening criteria stored in memory. Otherwise, the process outputs a negative patient status (121). Optionally, the resultant patient status may be registered in the associated system or network (see e.g., FIGS. 2A-2C), associated with the patient in real-time, and indicated on the acuity dashboard (125).

With a positive Systemic Inflammatory Response Syndrome determination, the process advances to the second stage 130. In this stage 130, the health care provider, as user, provides clinical judgement-based input to the process and to a system algorithm for determining a "high" probability of end organ damage due to infection (noting that "high" in this context is not a relative value or degree but simply a title given for the positive determination). As discussed previously, the detection or selection of any one of a set of criteria determines a positive patient status for high probability of end organ damage due to infection. Otherwise, the absence of such detection or selection determines and outputs a False Positive patient status (131). Optionally, that resultant patient status may be registered in the associated system or network, associated with the patient in real-time, and indicated on the acuity dashboard (125).

With a positive determination of a high probability of end organ damage due to infection, the process advances to the third stage (130), in which the presence of severe or actual end organ damage due to infection is tested. In this stage, clinical parameters are provided, through user selections, as input to the appropriate algorithm. If any one of a set of criteria is detected or selected, end organ damage due to infection is determined. Otherwise, a negative patient status is outputted and the presence of Systemic Inflammatory Response Syndrome is identified with the patient (141). As before, that patient status may be registered in the associated system or network, associated with the patient in real-time, and indicated on the dashboard (125). In the alternative, upon the process output of the presence of end organ damage due to infection (142), that patient status may be registered in the associated system or network, associated with the patient in real-time, and indicated on the acuity dashboard (125). As a further option, the process may initiate one or more notification actions (150).

In one aspect, a system and method disclosed herein entails or incorporates the integration of a plurality of sources of patient-specific data and parameters related to the patient's medical conditions and status to create a knowledge base of patient data. These data sources may include: reports by health care providers on observations made at bedside; electronic medical records; and data from monitors and sensors (e.g., at the patient's bedside or at a remote location, or if directly attached to the patient). In another aspect or feature, the system or method provides for intelligently presenting patient data to the health care provider throughout an iterative analysis and, in which, the most current and accurate patient data is presented.

In yet another aspect or feature, a system and a method are described having the capability of identifying patients with Systemic Inflammatory Response Syndrome (i.e., a precursor to sepsis), providing the health care provider the information to determine if a patient has a significant suspicion or risk of infection or alternative explanations for non-infectious causes of Systemic Inflammatory Response Syndrome, and\or using the precursor information to guide the health care provider in an intelligent screening of the patient.

In one aspect, a computer implemented method of screening a patient with possible medical condition(s) is provided wherein the Application's algorithm(s) determine whether sufficient conditions are present to have a high likelihood of the targeted medical condition and then identifying that patient as having a high risk of the medical condition. The method further provides recommending an intervention plan for the patient including recruiting and assigning health care providers as needed for execution of the intervention plan, and iteratively analyzing patient data and recalibrating the intervention plans as necessary.

In another aspect or feature, a system or method is described providing hardware/software platform-independent delivery and a user interface customizable to the specifics of the situation including those of the user facility and that of the patient and the patient's medical condition. Further, the system or method features, in certain embodiments, diagnosis or patient screening algorithms that may be customized by integrating a human health care worker's job-specific work-flow into the system or method for real-time screening, diagnosis, and management of a given medical condition. For example, screening algorithms may be customized for an advanced practice registered nurse whose work flow differs from that of a bedside registered nurse in a typical hospital environment. The system or method may further include the capability of:

allowing supervising health-care providers to audit a patient population for whether or not screening has been performed;

allowing users the option to de-selects parts of the process algorithm to better reflect the unique requirements of a patient, thereby decreasing false positives and increasing positive predictive values;

deriving a real-time characterization of the patient census based on the patient's acuity of illness to prioritize and triage the patients identified with Systemic Inflammatory Response Syndrome or suspicion of infection or other medical conditions and to enable medical intervention based on comparative acuity between that patient and all others present in that facility in order to facilitate effective use of resources and staff;

effectively "learning" and adapting the system or method to the individual patient based on specifics of that patient including that patient's pre-existing medical conditions, current status, and evolving disease status; and customizing sepsis screening or management of a given medical condition based on that patient's individual disease condition.

The system and Application according to the disclosure also provides a customizable, domain-specific user interface(s). The user interface is designed for health care providers and to lead them in an intuitive manner through a system or method of screening, diagnosing, and managing severe infections. The graphical user interface is further designed for efficient and effective data entry and analysis throughout screening, diagnosing, and managing of a patient. This point alone should reduce, if not eliminate, the typical initial tendency of a user toward a manual system or a workaround over an automated system (i.e., because of a perceived cumbersome and inflexible nature of the automated user interface).

The systems and processes disclosed herein also has the further capability of being integrated with industry standard electronic medical record systems, allowing health-care providers to assign patients with a given disease state to themselves and follow the patients' progress during the course of the shift. The system and process also allows for automatically updating the patient's electronic medical record to place orders for tests including but not limited to laboratory or radiographic tests.

Figure 2A:
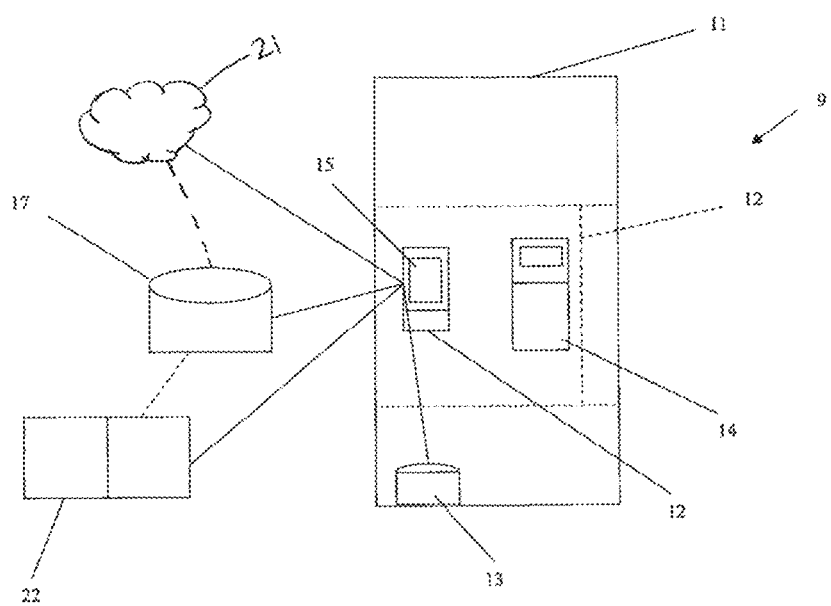
FIG. 2A is a simplified diagram illustrating an exemplary system for or through which one or more steps of the method of FIGS. 1, and 1A-1E may be performed, in accordance with an embodiment of the present disclosure.
Figure 2B:
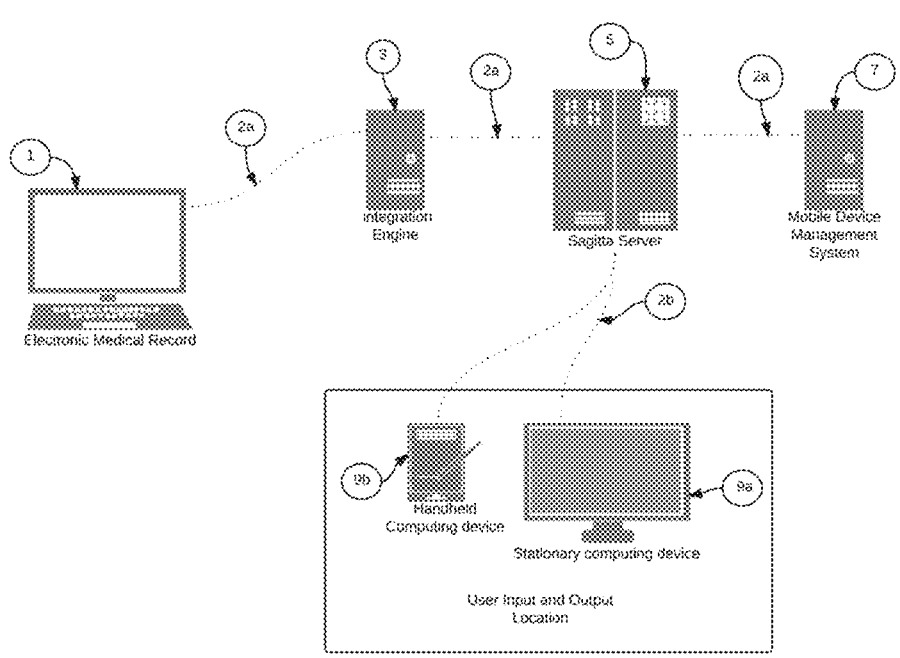
Figures 2C, 3A:
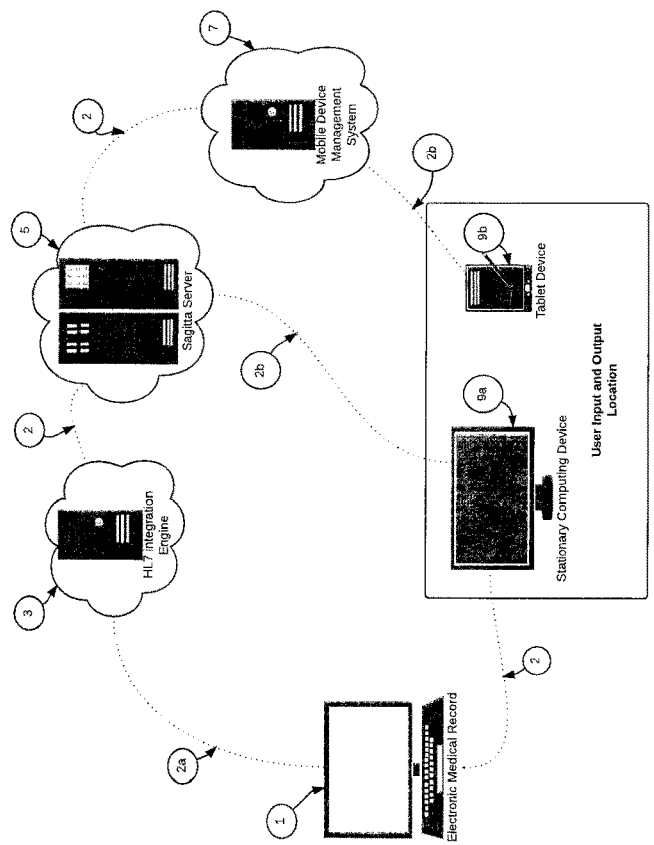

Each of FIGS. 2A-2C depicts an exemplary system in which and by which the process(es) of FIG. 1 may be carried out (with like reference numerals used to indicate like elements). In one respect, the system comprises an input\output device, preferably a computing device, a server, a patient information database, and\or a cloud network. In a preferred embodiment, the computing device is a handheld computing device with user input means and output means. For example, the computing device may be a smart phone, tablet, notebook, laptop, or similar device. The input means includes a user responsive hardware interface having a keyboard or touch screen, as well as the standard array of communication ports and wireless interfaces. Preferably, the process description associated with FIG. 1 contemplates communicating through a voice activated and\or touch screen user interface. Suitable output means includes a conventional display and\or communications interface for connecting to a local or cloud network (including dedicated servers).

Implementation of the method in preferred embodiments provides one of several results or diagnoses. In one implementation, the method provides for or determines the apparent absence of Systemic Inflammatory Response Syndrome. In another or further implementation, the method provides a positive diagnosis of, and more specifically, a high probability of end organ damage due to severe infection. In yet another or further implementation, the method provides a positive diagnosis for end organ damage due to infection. In more specific implementations described below and illustrated by the flowcharts of FIGS. 1A-1E, the method provides a positive sepsis diagnosis, and more specifically, a high probability of sepsis or severe sepsis. Alternatively, the method may provide a false positive sepsis diagnosis. The method may, in fact, calculate a false positive sepsis diagnosis, just as an experienced and expert human health care provider may provide. It is expected, however, that implementation of the systems and methods according to the present disclosure will present a significantly smaller number of false positives than conventional systems and methods.

The flowchart 1000 of FIG. 1A-1E describes, in more detail, an exemplary method(s) of screening according to the present disclosure and specifically, screening a patient for sepsis according to a preferred embodiment. The method may be characterized as being implemented systemically or, as well, by medical personnel utilizing a hand-held or locally stationed computing device. The computing device includes and communicates with a resident (on-site at a facility hosting the patient) or remotely located processor(s) and memory storing programmable instructions executable to initiate or perform various steps in the process. These programmable instructions are packaged in a software application (Application) that can be initiated from or in the computing device. In any event, the computing device enables interactive graphical user interfaces to the software application responsive to input by the user and capable of projecting output displays and other activity generated by the Application, as described herein.

The process includes a series of user-prompted determinations which, if result in a series of affirmations, outputs a sepsis diagnosis. Each of the determinations is made through user interaction with three menu graphical user interfaces or screens—Screen 1, Screen 2, and Screen 3. Each Screen receives inputs (directly from user or from system) and runs an algorithm to output the determination. More specifically, each screen presents or prompts a set of user selections and the user responses or selections is received as patient data input to the algorithm. The method is initiated with activation of the computing device having a touch based interface (1002). Typically, the user or users will have the device at hand and will be physically present in a hospital or clinic environment attending to a patient (although such physical proximity or direct contact is not necessarily required). Furthermore, the device may be connected to a cloud network either wirelessly or hard wired. Preferably, the user securely logins with a password or biometric scanning to maximize security.

In a preliminary step (1004), patient information is accessed and loaded for the patient. The patient's screening record may be accessed by: census retrieval from the server; scanning a patient wrist band; manual input; and accessing previous patient log. In another aspect of the present disclosure, when the patient is assigned to a specific health care provider, that health care provider's total group of patients is preferably displayed on an acuity-based electronic "dashboard." An acuity dashboard, such as one depicted in FIG. 6 and discussed below, provides and identifies for the health care provider, among other things, the screening status of patients (e.g., whether patients have been screened or still require screening).

In one process application, the user proceeds to take the patient's vital signs and enters the information obtained via the device interface as input into the software application. Typically, the vital signs collected and inputted include:
1. Blood pressure—Systolic and Diastolic
2. Temperature
3. Respiratory Rate
4. Peripheral capillary oxygen tension/saturation
5. Blood Glucose level The application then pushes the data to the electronic medical record securely.

In a further aspect, the application also indicates to the user whether the value is normal or abnormal, for example, by presenting the screen background in red (as opposed to normal background color) or by employing some other alert. The Application typically provides an input screen by which the values collected may be entered by either turning a dial or moving a slider. Alternatively, the values may be selected on the touch interface and then manually entered. In any event, the Application significantly improves the process of data entry by eliminating the need to transcribe vital signs from the patient's bedside onto paper and then entering it into the computer.

In one aspect, the Application provides Screen 1 for a user-prompted determination based on physical measurements or measurements of the patient (1006). The procedure may determine, in the converse, the absence of Systemic Inflammatory Response Syndrome, thereby prompting the user to return to the main or native screen. As shown in the flowchart, Screen 1 presents to the user as queries and\or for selection by the user (or system), multiple possible patient condition parameters (Systemic Inflammatory Response Syndrome criteria). The user responses are received as input and the method runs an algorithm based on the input to determine patient status (1006). In accordance with the present disclosure, a user finding and menu selection of at least two of the presented variables leads to an intermediate diagnosis. The menu selections available on Screen 1 are printed in TABLE 1 below.

TABLE 1

SCREEN 1 SELECTIONS

| | |
|---|---|
| A. | Temperature greater than 100.1 less than 96.8; |
| B. | Heart rate greater than 100 bpm or less than 60 bmp; |
| C. | Respiratory rate >20 breaths per minute; |
| D. | Having a new alteration of mental status or a toxic appearance; |
| E. | Laboratory values of white blood cell count greater than twelve thousand per ml or less than 4 thousand per ml or >10% bands; |
| F. | Blood glucose less than 60 mg/dl or more than 160 mg/d; and |
| G. | None of the Above. |

If the user (human health care provider) does not observe any of the patient condition parameters as present in the patient, the user may select "none of the above" (as the Application input). The patient is effectively screened and the Application updates the system's knowledge base accordingly. The Application then displays "screening complete" complete. Upon the user hitting "OK", the Application returns to the native screen. Further, if the Application's algorithm does not calculate the targeted condition being present (or the user provider selects the "none of the above" as above), the Application displays a "SYSTEMIC INFLAMMATORY RESPONSE SYNDROME ABSENT" screen (or equal) (1006a) before returning the user to the native screen. If the Application calculates, using the appropriate algorithm, that sufficient medical conditions are selected, the Systemic Inflammatory Response Syndrome screening criteria are met and the Application displays an alert stating "Systemic Inflammatory Response Syndrome present" (1006b). In the application according to FIGS. 1A-1E, the observation or selection of two or more condition parameters by the user indicates that the Systemic Inflammatory Response Syndrome screening criteria are met, thereby prompting display of the "Systemic Inflammatory Response Syndrome present" alert (1006b). Upon a user-activated prompt, the Application sends the server a label with a time stamp of "Systemic Inflammatory Response Syndrome present" (for that patient), which is then saved in the analytic server's database.

The Application now advances to Screen 2 (1010). Screen 2 enables the system to further adjust the sensitivity of screening based on numerous pre-test probability conditions. Each of the conditions in TABLE 2 below is provided as user selections on Screen 2.

TABLE 2

SCREEN 2 SELECTIONS - CLINICAL JUDGEMENT

| | |
|---|---|
| A. | Suspicion of Infection (Clinical judgment); |
| B. | Recent Antibiotic administration (Past Clinical Judgment); |
| C. | Recent procedure (increases probability of invasive infection); |
| D. | Presence of indwelling lines or catheters (increases probability of invasive infection; |
| E. | Positive blood cultures (increases probability of invasive infection); and |
| F. | None of the Above. |

Figure 1C:
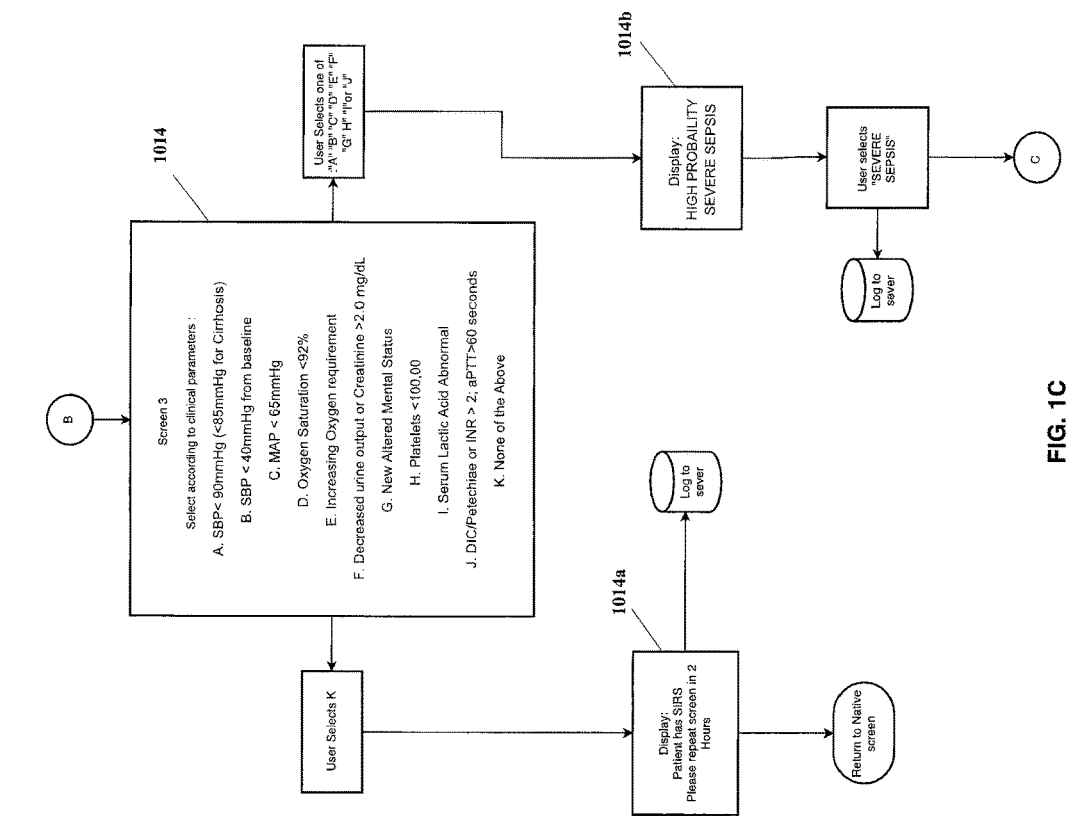
Figure 1B:
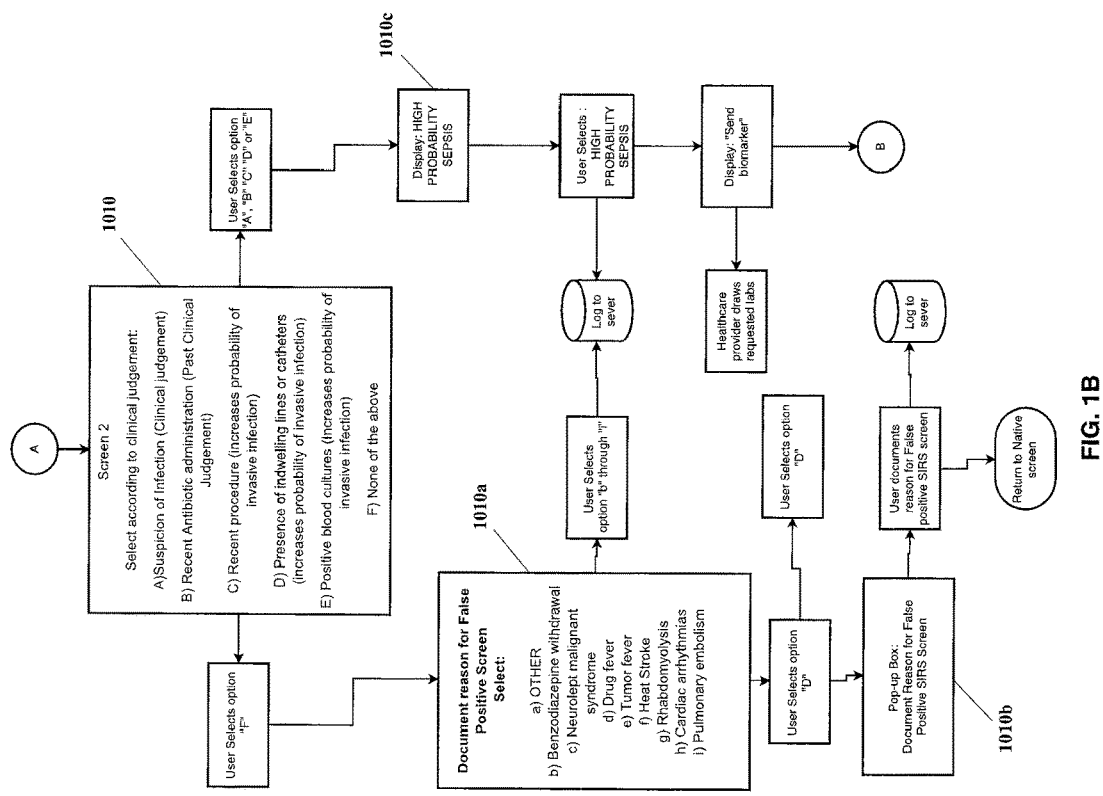

As shown in FIG. 1B, a "none of the above" user selection results in the system presenting a False Positive diagnosis. A new user selection False Positive Screen is then presented with the menu of selections in TABLE 3 below (1010a).

TABLE 3

FALSE POSITIVE SCREEN SELECTIONS

| | |
|---|---|
| A. | OTHER; |
| B. | Benzodiazepine withdrawal; |
| C. | Neurolept malignant syndrome (NMS); |
| D. | drug fever; |
| E. | tumor fever; |
| F. | heat stroke; |
| G. | rhabdomyolysis; |
| H. | cardiac arrhythmias; and |
| I. | pulmonary embolism. |

The above menu provides possible reasons or sources for the False Positive diagnosis. If the user selects OTHER, the system provides a pop-up screen in which the user can manually insert a reason for the False Positive (1010c).

In one example, a "Subject A" is screened and results in a False Positive diagnosis. A reason for the False Positive, e.g., "Reason X", is selected as discussed above and stored in the system (in the analytic server's database). If screening of Subject A is undertaken at a later time and arrives at Screen 1, and the same parameters as before are selected, the Application will present the query "Does the patient still have "Reason X"?." This query substitutes the usual display, "Systemic Inflammatory Response Syndrome Present", and may avoid the user having to go through Screen 2 and rendering another "FALSE POSITIVE" diagnosis. If "YES" is selected, then the Application displays the notification: "Patient previously tested False Positive for Systemic Inflammatory Response Syndrome due to "X" and prompts the user to further select either "CONTINUE" or "FINISH SCREENING." If "Continue" is selected, the process advances to Screen 2 as before. If "FINISH SCREENING" is selected, the results are submitted to the server and the Application returns to native state.

In the alternative, if different parameters are selected on Screen 1 for Subject A, the program will display "Systemic Inflammatory Response Syndrome present." On Screen 2 for "Subject A", a clickable link is presented indicating that the patient had a previous False Positive Systemic Inflammatory Response Syndrome and when, activated, the "Reason X" will appear in a popup window. An "OK" button will also appear which, when selected, returns the process to Screen 2 for "Subject A."

Returning to Screen 2, if one or more conditions A through E are selected, the Application will display the further diagnosis "High Probability Sepsis Present" in a window, which the user must activate (1010c). The user is then instructed to "Send Venous Lactate" with options "OK"

and "Defer." Upon user selection of "Send Venous Lactate," the Nurse or other healthcare professional is prompted to send a blood sample of Venous lactate from the patient. Upon selection of either "OK" or "DEFER", the server is sent a label with a time stamped "High Probability Sepsis Present" notice (for that patient). This information is also saved in the log.

As shown in FIG. 1C of the process, the user advances to Screen 3 after the "High Probability Sepsis Present" diagnosis (1014). At Screen 3, the Application runs an algorithm that receives user-selected clinical parameters as input and then screens the patient for signs and symptoms of Severe Sepsis (1014). The user is presented the menu of conditions for selection in TABLE 4 below.

TABLE 4

SCREEN 3 USER SELECTIONS - CLINICAL PARAMETERS

| | |
|---|---|
| A. | SBP <90 mmHg (<85 mmHg for Cirrhosis) |
| B. | SBP <40 mmHg from baseline |
| C. | MAP <65 mmHg |
| D. | Oxygen Saturation <92% |
| E. | Increasing Oxygen requirement |
| F. | Decreased urine output or Creatinine >2.0 mg/dL |
| G. | New Altered Mental Status |
| H. | Platelets <100,000 |
| I. | Serum Lactic Acid Abnormal |
| J. | DIC/Petechiae or INR >2; aPTT >60 seconds |
| K | None of the Above |

Key:
SBP—Systolic Blood pressure
MAP—Mean Arterial Pressure
DIC—Disseminated intravascular coagulation If the user selects Option K ("None of the Above"), the Application displays in a popup window, "Patient is Systemic Inflammatory Response Syndrome" and "Please Repeat Screen in 2 hours" (1014a). With the user's approval, the Application sends the screening results information to the server and returns to native state. If the user opts to select "CANCEL", the Application returns to Screen 3.

Otherwise, if the user selects of one or more of Options "B" through "J", a diagnosis of "HIGH PROBABILITY OF SEVERE SEPSIS" is made and a corresponding display notification is provided (1014b). The Application then advances as shown in FIG. 1D and queries the user. Specifically, the user is presented a popup menu of available system notification activities (1018), including the following menu options:

1. SEPSIS Nurse
2. Pharmacy
3. Bed Control
4 Charge ICU Nurse
5. ICU on call MD

Upon selection of one or more of options, the system sends, via the server, the appropriate alphanumeric page to the designated personnel (1020). The Application then presents a menu (1022) displaying the following instructions:

1. Blood culture×2
2. Administer broad spectrum antibiotics within 60 minutes
3. Bolus 30 ml/kg N.S IV unless contraindicated When the above instructions are fulfilled, the appropriate prompts on the display may be checked, and when checked (i.e. activating "OK"), the patient information is sent to the server. Furthermore, if the user wishes to recall the alert (after fulfilling instructions), an "ISSUE RECALL" notice may be prompted to send a second page cancelling the previous message. The Application then returns to native state.

Figure 1E:
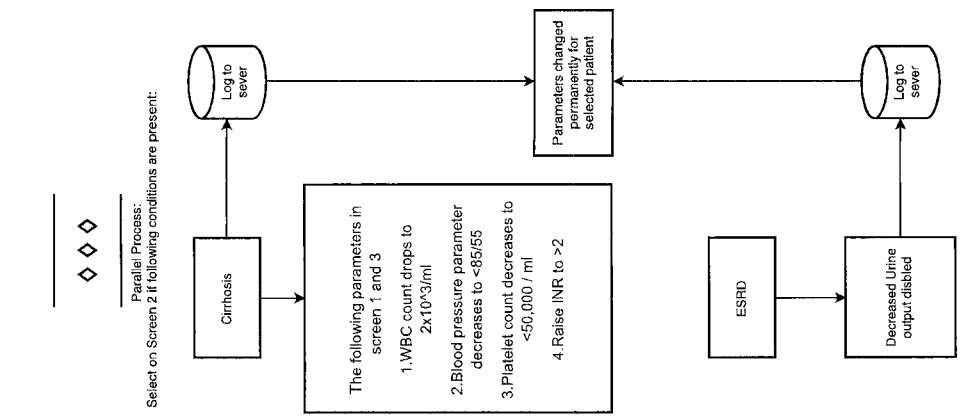
Figure 1D:
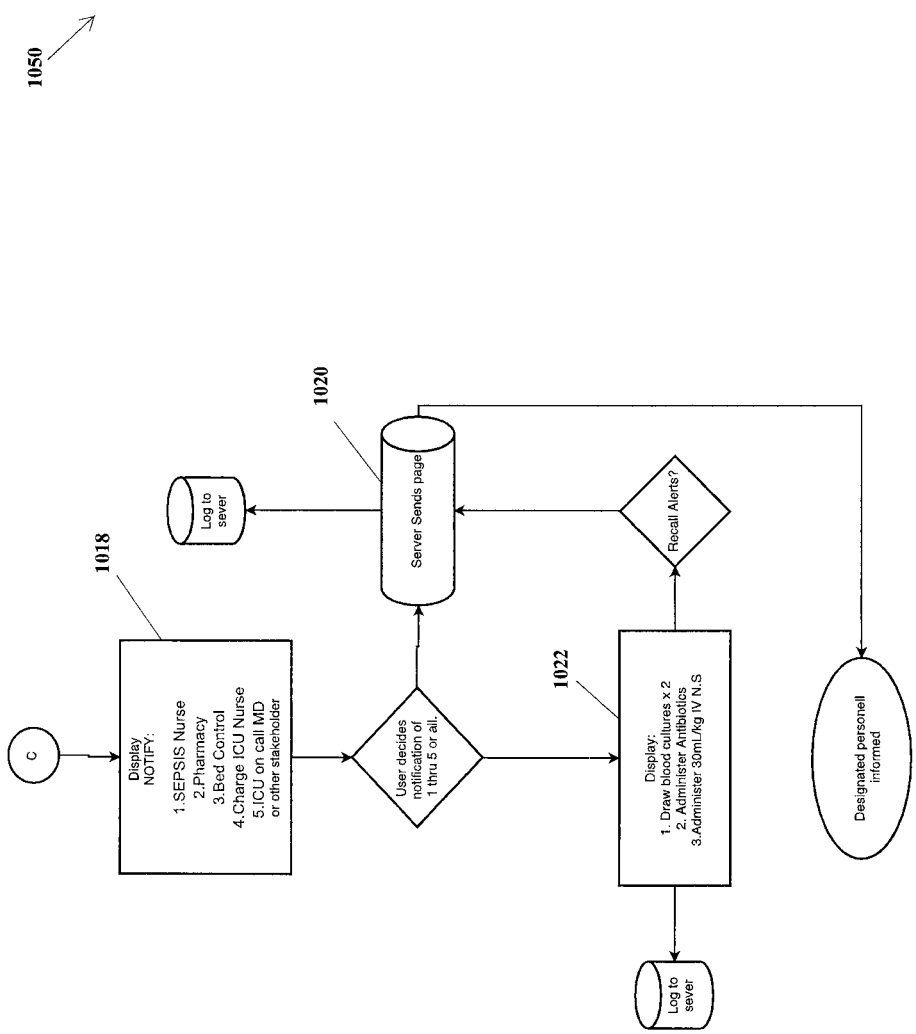

The flowchart section (1050) of FIG. 1E represents a parallel process stemming from Screen 2 and accounting for patient conditions of Endstage Liver Disease/cirrhosis (ESLD) and Endstage Renal Disease (ESRD). This parallel process is initiated upon a user selection of "A" in Screen 3. The following parameters in Screens 1 and 3 are changed if the user indicates that the patient has Endstage Liver disease/cirrhosis (ESLD):

1. WBC count drops to $2 \times 10^{\wedge}3$/ml;
2. Blood pressure parameter decreases to <85/55;
3. Platelet count decreases to <50,000/ml;
4. Disseminated intravascular coagulation (DIC) selection is disabled; and
5. International Normalized Ratio raised to 3.

The following parameters in Screen 3 are changed if the user indicates that the patient has endstage renal disease (ESRD):

1. Decreased urine output selection is disabled.
2. Creatinine is ignored in all parts of the algorithm The following table summarizes the adjustments to the Application Screens:

TABLE 5

ESLD/ESRD SCREEN OPTIONS

| | |
|---|---|
| | Nuances for ESLD: (see FIG. 1E) |
| 1. | Option "A" will be decreased to <85 mmHg |
| 2. | Option "H" will be decreased to <50,000 |
| 3. | Option "J" will be disallowed |
| | Nuances for ESRD: (see FIG. 1E) |
| | Option "F" will be disallowed |

In one embodiment, a system 9 according to the disclosure includes a computing device 10 as shown in FIG. 2 and as discussed above, configured for operation by one or more patient care personnel through a graphical user interface 15. Preferably, at certain stages of the process, the computing device 10 is operated within a patient care facility 11 (e.g., hospital), and more specifically, proximate a subject or patient 14 identified for screening (e.g., within a patient room 12). The patient care facility 11 may include a local network including a patient database 13 provided in communication with the computing device 10. The system 9 may further include a server 17 located remotely from the computing device 10, which may be configured with or as part of a cloud network 21. In this example, a database 22 is also included and similarly configured, as shown in FIG. 2. The database 22 may store patient-related or screening-related information inputted or logged as illustrated in the flowchart of FIG. 1.

Each of FIGS. 2B-2C depicts further preferred systems 200 in which and by which the process(es) of FIG. 1 may also be carried out, with like reference numerals used to indicate like elements. In FIG. 2B, the system 202 provides and\or incorporates a local network, while the system 202 of FIG. 2C provides and\or incorporates a cloud-based network. The system 200 includes one or more input\output devices, preferably handheld computing device 209a and\or stationary computing device 209b, a server 205, a patient information database 201, an integration engine 203, and a mobile device management system 207 that manages handheld computing devices 209b. In a preferred embodiment, the computing device is a handheld computing device with user input means and output means. For example, the computing device may be a smart phone, tablet, notebook, laptop, or similar device. The input means includes a user responsive hardware interface having a keyboard or touch screen, as well as a standard array of communication ports 202a and wireless interfaces 202b. It is contemplated that the processes described herein, including those described in respect to FIGS. 1 and 2, may communicate through a voice activated and\or touch screen user interface. Suitable output means includes a conventional display and\or communications interface for connecting to a local network or cloud network (including dedicated servers), as required.

Any number of commercially available mobile devices is suitable for use with the system and processes described. These include such devices having a touch-based interface, including such products referred to as ipad, iphone, android tablets, and touch-based laptops. The mobile device is preferably connected to a wireless network for securely login. In an initial step, the patient's medical record is accessed by and through the device, and\or by scanning armband from camera, manual input, census retrieval for server, previous patient history from log on device. If the option is unavailable, the device and the process of information collection according to the present disclosure, presents the user the option to retry or else grey out option and employ any other three options to access the patient's data.

FIGS. 3A-3D provide illustrative examples of graphical user interfaces through which or by which certain steps of the process may be performed. These user interfaces include input and output means for communicating object data and information as discussed above in respect to the flowchart of FIG. 1. These user interfaces are particularly applicable for use on a handheld device such as a smartphone or digital tablet. The user interface 300 of FIG. 3A may correspond to the "Load Patient Information" screen or step in FIG. 1, which is used to initiate screening. The user interfaces 320, 330 of FIG. 3B or 3C may correspond with or provide Screen 1 of the process. Notably, screen 330 on FIG. 3C indicates certain patient parameters inputted for the Anonymous Patient. The system then outputs a notice to the user based on the indications in FIG. 3C. As discussed above, the presence of two Systemic Inflammatory Response Syndrome criteria/parameters triggers a "Systemic Inflammatory Response Syndrome Patient" notice and display.

Table 6 provides additional, exemplary graphical user interfaces suitable for use with the systems and methods described herein, including the method/process according to FIGS. 1A-1E.

TABLE 6

GRAPHICAL USER INTERFACES

| | |
|---|---|
| 1. | "SCREEN 2" 410 (FIG. 4A) (with user selection options presented) |
| 2. | Output Screen 420 (FIG. 4B) (with one user selection inputted) |
| 3. | Output Screen 430 (FIG. 4C) (with two affirmative user selections prompting positive patient status - high probability of sepsis) |
| 4. | "SCREEN 3" 510 (FIG. 5A) |
| 5. | Output Screen 520 (FIG. 5B) |
| 6. | Output Screen 530 (FIG. 5C) |
| 7. | Abort/Exit Screen (FIG. 5D) |

The presently described systems and processes aims to identify patients with a high risk of end-organ damage due to severe medical conditions and further, provide a health care provider with decision support. This may entail providing pre-populated vital signs or calculating shock index to determine if the patient has SIRS, where shock index is calculated by a standard industry practice of dividing the heart rate by the systolic blood pressure, and also pre-populating laboratory and other pertinent clinical data. Preferably, this support eliminates the need for the health care provider to comb through data that is not pertinent to the patient's severe medical condition. The method of decision support may also include explaining and documenting common medical factors that, previously, would have led to misdiagnosing the severe medical condition, so as to reduce false positives and increase positive predictive value of the computing system iteratively. Support recommendations are maintained in the patient's electronic medical record and in the database.

For example, a patient may suffer end-organ damage (severe medical condition) due to infection, but the patient originally presents with a non-infectious cause for SIRS (false positive for infection) and, correctly, is not given antibiotics. Later, the patient develops SIRS that is from an infectious cause and at this later date has a delay in administration of antibiotics due to the health care provider not having noticed the appropriate markers of a new and developing condition (that was not present initially). To illustrate further, a patient may have a fever to 101 F and has a tachycardia with a heart rate of 120, and is diagnosed as having SIRS. The patient is considered as being free of any clinical signs or focus of infection on laboratory or radiographic studies, according to the experienced health care provider. The patient has an inflammation of the pancreas (pancreatitis) that frequently causes fever and tachycardia. The nurse marks that the patient has non-infectious SIRS secondary to pancreatitis. A few days later, the patient develops an elevated white blood cell count with elevated "band forms" (immature white blood cells—an indicator of new or developing infection) and has a decrease in blood pressure (resulting in a high shock index). The patient is correctly identified as having a second SIRS state which is different from the initial state. The nurse is able to effectively recruit assistance from a physician to order antibiotics and a pharmacist to bring those antibiotics to bedside in a time manner.

With current technology, this patient would have continued for more than eight hours without appropriate treatment due to an anchoring heuristic resulting in an increased mortality and harm to the patient (literature shows that mortality increases by 7% for every hour of delayed administration of antibiotics ref: Kumar et al, 2007.) This present system and process minimizes false positives and maintains that information so that if the patient develops infection-related to SIRS and presents legitimate symptoms at a later time, the patient is correctly diagnosed with infection-related SIRS.

Implementation of the presently disclosed systems and processes with conventional screening and treatment processes currently employed is expected to achieve certain benefits, including reduction in mortality rates, cost, and lengths of patient stay in the hospital. There is also an expected reduction in response time to a patient who meets criteria based on the system's alert protocols. This prevents escalation from sepsis to severe sepsis and/or septic shock for "at-risk" patients after hospital admission due to delay in treatment.

There is also an expected improvement in data management by using templated notes-ability to import sepsis log and post to patient's medical record to complete the heath care provider's documentation. Furthermore, quality improvement mechanisms are made more agile by real time data reporting, which allows for on-the-fly review of data (no need for onerous chart review) and shorter plan-do-study-act (PDSA)cycles for quality improvement. This is especially important since adherence to sepsis bundles is reportable starting September 2015

There may also be numerous benefits to the health care provider. For example, the presently disclosed systems and processes should aid in preventing "Algorithm Agnosia"—a condition in which the health care provider discounts or fails to recognize a true positive event due to repeated prior false alarms. Implementation of the presently disclosed system and process should also aid in process normalization within the hospital by reducing variations of care, decrease telemetry utilization by frequently screening high risk patients on non-telemetry floors, and prevent inaccurate assessments of patients on transferring from one level of care to another (e.g., emergency room to the floor instead of emergency room to intensive care unit).

The following is a description of a system by which data is extracted from the electronic medical record and then independently processed to achieve desired output.

Examples

1. Sepsis Screening: Output data of whether patient is septic or not based on Systemic Inflammatory Response Syndrome plus lab/radiology input from EMR 2. Clinical optimization of end-stage heart failure patients for assist device implantation or heart transplantation—data processing uses analysis to determine what next steps the clinician must take to optimize the patient for assist device implant (e.g., if an obese patients who was previously excluded from transplant for morbid obesity, starves themselves and BMI drops from 30-28 between clinic visits but pre-albumin level also drop the program will indicate to the provider that a nutrition evaluation is necessary and that the clinically significant drop in BMI indicates a deterioration in health rather than the person getting closer to being a candidate for transplant.

3. Transfer evaluation for higher level of care: in a non-tertiary care hospital the entire hospital census is analyzed on a real-time basis and an acuity score is calculated for each patient.

Based on the acuity score, each patient will be evaluated for benefit of transfer to a higher level of care, e.g., a patient with elevated bilirubin, elevated AST/ALT, INR>2.0 and platelet count<100,000 will benefit from transfer to a higher level of care for liver transplant evaluation. This data will be presented to the attending physician with the option to refer the patient to a medical center where a hepatologist is available. If the doctor accepts the face-sheet and insurance details are automatically pushed to both transfer centers (accepting and sending facilities). The on-call consultant and hospitalists are notified electronically and clinical data is presented to them. If the patient is deemed appropriate for transfer a doctor to doctor conversation is initiated automatically via the transfer center between all three providers. This system streamlines the existing workflow and ensures that patients who would benefit from higher level care are provided the best care available.

The above provide some examples. It should be apparent however to one skilled in the art that a framework is provided that allows clinicians to build any sort of query algorithm to process data on a real-time basis.

Sepsis is a general term used to describe a syndrome that occurs when the body's immune system overreacts to a local infection, resulting in uncontrolled system-wide inflammation. Undiagnosed sepsis is a significant threat to patients' well-being, as well as a major drain on the time, energy and resources of healthcare institutions. Several independent studies have shown that screening for sepsis reduces mortality rates in hospitalized patients. Use of the presently described systems, process, and graphical user interfaces will aid in streamlining sepsis care in acute care facilities and decreasing mortality rates, costs and length of stay. A protocol utilizing the presently disclosed systems and processes implements a sustainable sepsis screening based on related algorithms for acute care hospitals. The protocol uses real-time data import from several sources and interacts directly with team members and processes including: the bedside nurse, nursing assistant, pharmacy, the hospital sepsis team, bed control. As statistically based measurement and standardization are often cited as the first steps to improving quality, the present systems and processes lend themselves to such improvements.

In preferred embodiments, the system and process utilized tablet-based bedside software. As it is server-linked, the tablet device provides real-time clinical decision making support. By providing real-time data to hospitals on acuity, incidence of Systemic Inflammatory Response Syndrome/sepsis and severe sepsis, one can control positive predictive value. The systems and processes allows, therefore, for more agile processing and customization to individual facilities.

Sepsis screening is tailored for patients with pre-existing organ system pathology. With the presently disclosed system and processes, including the Application, one can modify individual variables to account for end-stage liver disease (ESLD); atrial fibrillation; heart failure; end-stage renal disease (ESRD), ventricular assist devices (LVAD and RVAD), balloon pumps and ventilators.

A suitable mobile or hand-held device for use with the presently disclosed systems and processes is any one of a number of commercially available mobile devices having a touch-based interface, including such products referred to as ipad, iphone, android tablets, and touch-based laptops. The device is preferably connected to wireless network to securely login. In an initial step, the patient's medical record is accessed by and through the device, and further by scanning armband from camera, manual input, census retrieval for server, previous patient history from log on device. In a typical operation, the camera input is a preferred first choice for access. If the option is unavailable, the device and the process of information collection according to the present disclosure, presents the user the option to retry or else grey out option and employ any other three options to access the patient's data.

Figure 6:
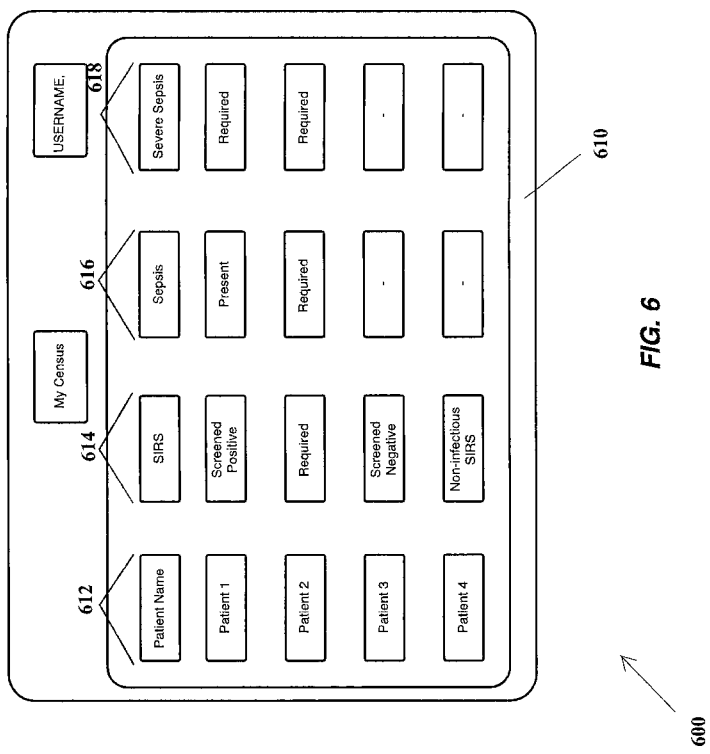
FIG. 6 is a representative graphical user interface for displaying an acuity dashboard for use with, or which may be generated by, the system and method of FIGS. 1 and 1A-1E, according to one embodiment of the present disclosure.

FIG. 6 depicts an exemplary graphical user interface 600 embodying and illustrating one example of an acuity dashboard 610 according to the present disclosure. The graphical user interface 600 may be provided on a handheld computing device, other mobile device, laptop, desktop, terminal, or other computing device preferably connected and in communication with the system(s) described herein, including those in FIGS. 2A-2C. Typically, the acuity dashboard 610 is unique to a health care provider-user and provides for that health care provider his\her patient census (groups of associated patients). In the acuity dashboard 600 of FIG. 6, information is conveniently provided in several columns, including a column 612 for Patient Name (i.e., patients assigned to the health care provider-user). The remaining columns (614, 616, 618) provide the patient's screening status for each of Systemic Inflammatory Response Syndrome, Sepsis, and Severe Sepsis. The patient status information is, of course, preferably delivered and updated, in real-time, by and from operation of the hand-held devices and Screens 1-3 described in respect to FIG. 2, for example.

Referring to the acuity dashboard of FIG. 6, Patient 1 is shown having been screened (using Screens 1 and 2) to determine the presence of Systemic Inflammatory Response Syndrome and the presence of Sepsis. Patient 1 is also shown as (still) requiring screening (using Screen 3) for Severe Sepsis, as prompted by a positive result in the screening to sub-process using Screen 2. In contrast, patient status for Patient 3 shows that the patient as being screened negative for Systemic Inflammatory Response Syndrome and thus not requiring further screening. Similarly, Patient 4 is shown not requiring further screening as well due to a scenario, for example, described below is Usage Scenario 4.

The following are exemplary Scenarios wherein an acuity dashboard and one or more processes as previously described are embodied and utilized in an Application. The process steps may be performed by user(s) with a handheld device or other computing device as previously discussed, and by or through a system or network as also previously discussed. The hardware system or network and\or software application is referred to as the Application for purposes of description.

Usage Scenario 1: New patient entered into system and Application calculates a high probability of sepsis.

Health Care Provider starts Application on device.

Health care Provider accesses hospital census from Application and adds new patient to their list (this patient is not yet on the list of previously screened patients).

The initial acuity dashboard screen presents the following comparative information for the Health Care Provider to consider, where the comparison is being made relative to other patients on that user's list of patients while calculating probability for that individual patient:
  a. Presence of high probability Systemic Inflammatory Response Syndrome by displaying "Required Screening" under Systemic Inflammatory Response Syndrome column
  b. Presence of high probability of infection by evaluating surrogate markers of infection by displaying "Required Screening" under Sepsis column
  c. Indicating whether or not biomarker labs are required or have already been sent in the "Biomarker" column by indicating "required" or "sent" or "resulted" respectively
  d. Presence of high probability of end-organ damage due to infection by displaying "Required Screening" under Severe Sepsis column The Health Care Provider then selects the patient to further evaluate the reasons for Systemic Inflammatory Response Syndrome, presence of infection and presence of end organ damage due to infection by initiating the screening process.

Application calculates based on the user's input and validation of the information presented via the user interface to determine the presence of Systemic Inflammatory Response Syndrome, Infection and end organ damage due to infection.

The dashboard screen now presents to the Health Care Provider the following information:
  e. Presence of verified high probability of Systemic Inflammatory Response Syndrome by displaying "Present" under Systemic Inflammatory Response Syndrome column
  f. Presence of infection being the cause of Systemic Inflammatory Response Syndrome by displaying "Present" under Sepsis column
  g. If the lab test has been sent it will display "sent" or "resulted" depending on if the lab test is available for review (resulted) or is still under processing (sent). It will further determine if the lab value is "normal" or "abnormal" and will display the same under column "Biomarker".
  h. Presence of end-organ damage caused by infection by displaying "Present" under the Severe Sepsis column The Health Care Provider then sends alerts stating "Sepsis present" to the other health care providers involved in the patient's care via Application which may interface to existing pagers, smartphones or text based messaging devices.

Usage Scenario 2: New patient entered into system and Application calculates a low probability of sepsis because the patient does not have sepsis (true negative).
  1. Health Care Provider starts Application on device.
  2. Health Care Provider accesses hospital census from Application and adds new patient to their list (this patient is not yet on the list of previously screened patients).
  3. The initial acuity dashboard screen presents the following comparative information for the Health Care Provider to consider, where the comparison is being made relative to other patients on that user's list of patients while calculating probability for that individual patient:
     a. Presence of low probability Systemic Inflammatory Response Syndrome by displaying "Absent" under Systemic Inflammatory Response Syndrome column
     b. Absence of surrogate markers of infection by displaying "–" under Sepsis column
     c. Indicating that biomarker labs are not required by displaying "–" in the "Biomarker" column
     d. Presence of low probability of end-organ damage due to infection by displaying "–" under Severe Sepsis column
  4. The Health Care Provider in this case will not further screen this patient and thereby not require allocation of time or other resources to evaluate the patient.

Usage Scenario 3: Existing patient updated in system and Application calculates a high probability of sepsis.
  1. Health Care Provider starts Application on device.
  2. Health Care Provider reviews list of existing patients they have previously assigned themselves
  3. The initial acuity dashboard screen presents the following comparative information for the Health Care Provider to consider, where the comparison is being made relative to other patients on that user's list of patients while calculating probability for that individual patient who previously did not have sepsis:
     a. Presence of high probability Systemic Inflammatory Response Syndrome by displaying "Required Screening" under Systemic Inflammatory Response Syndrome column
     b. Presence of high probability of infection by evaluating surrogate markers of infection by displaying "Required Screening" under Sepsis column
     c. Indicating whether or not biomarker labs are required or have already been sent in the "Biomarker" column by indicating "required" or "sent" or "resulted" respectively
     d. Presence of high probability of end-organ damage due to infection by displaying "Required Screening" under Severe Sepsis column 4. The Health Care Provider then selects the patient to further evaluate the reasons for Systemic Inflammatory Response Syndrome, presence of infection and presence of end organ damage due to infection by initiating the screening process.
5. Application calculates based on the user's input and validation of the information presented via the user interface to determine the presence of Systemic Inflammatory Response Syndrome, Infection and end organ damage due to infection.
6. The dashboard screen now presents to the Health Care Provider the following information:
   a. Presence of verified high probability of Systemic Inflammatory Response Syndrome by displaying "Present" under Systemic Inflammatory Response Syndrome column
   b. Presence of infection being the cause of Systemic Inflammatory Response Syndrome by displaying "Present" under Sepsis column
   c. If the lab test has been sent it will display "sent" or "resulted" depending on if the lab test is available for review (resulted) or is still under processing (sent). It will further determine if the lab value is "normal" or "abnormal" and will display the same under column "Biomarker".
   d. Presence of end-organ damage caused by infection by displaying "Present" under the Severe Sepsis column
7. The Health Care Provider then sends alerts stating "Sepsis present" to the other health care providers involved in the patient's care via Application which may interface to existing pagers, smartphones or text based messaging devices.

Usage Scenario 4: New patient updated in system and Application calculates a low probability of sepsis because the patient has symptoms that could cause a false positive.
1. Health Care Provider starts Application on device.
2. Health Care Provider accesses hospital census from Application and adds new patient to their list (this patient is not yet on the list of previously screened patients).
3. The initial acuity dashboard screen presents the following comparative information for the Health Care Provider to consider, where the comparison is being made relative to other patients on that user's list of patients while calculating probability for that individual patient:
   a. Presence of high probability Systemic Inflammatory Response Syndrome by displaying "Required Screening" under Systemic Inflammatory Response Syndrome column
   b. Absence of high probability of infection by absence surrogate markers of infection by displaying "Required Screening" under Sepsis column
   c. Indicating whether or not biomarker labs are required or have already been sent in the "Biomarker" column by indicating "required" or "sent" or "resulted" respectively
   d. Absence of high probability of end-organ damage due to infection by displaying "–" under Severe Sepsis column
4. The Health Care Provider then selects the patient to further evaluate the reasons for Systemic Inflammatory Response Syndrome, presence of infection and presence of end organ damage due to infection by initiating the screening process.
5. Application calculates based on the user's input and validation of the information presented via the user interface to determine the presence of Systemic Inflammatory Response Syndrome, Infection and end organ damage due to infection. In this case the user determines that there is no infection present due to the absence of surrogate markers of infection. User selects a reason for Systemic Inflammatory Response Syndrome that is not related to infection.
6. The dashboard screen now presents to the Health Care Provider the following information:
   a. Presence of Non-infectious cause of Systemic Inflammatory Response Syndrome by displaying "Non-Infectious Systemic Inflammatory Response Syndrome" under Systemic Inflammatory Response Syndrome column
   b. Absence of infection being the cause of Systemic Inflammatory Response Syndrome by displaying "Absent" under Sepsis column
   c. If the lab test has been sent it will display "sent" or "resulted" depending on if the lab test is available for review (resulted) or is still under processing (sent). It will further determine if the lab value is "normal" or "abnormal" and will display the same under column "Biomarker".
   d. Absence of end-organ damage caused by infection by displaying "–" under the Severe Sepsis column
7. The Health Care Provider by selecting the reason for "Non-Infectious Systemic Inflammatory Response Syndrome" via this process modifies the parameters of that discrete patient in order that their Systemic Inflammatory Response Syndrome alert will not trigger for the same reasons as they triggered the initial alert. By this manner future false positives are avoided.

Usage Scenario 5: Existing patient updated in system and Application calculates a low probability of sepsis because the patient has symptoms that could cause a false positive.
1. Health Care Provider starts Application on device.
2. Health Care Provider reviews list of existing patients they have previously assigned themselves
3. The initial acuity dashboard screen presents the following comparative information for the Health Care Provider to consider, where the comparison is being made relative to other patients on that user's list of patients while calculating probability for that individual patient who previously did not have sepsis:
   a. Presence of high probability Systemic Inflammatory Response Syndrome by displaying "Required Screening" under Systemic Inflammatory Response Syndrome column
   b. Absence of high probability of infection by absence surrogate markers of infection by displaying "Required Screening" under Sepsis column
   c. Indicating whether or not biomarker labs are required or have already been sent in the "Biomarker" column by indicating "required" or "sent" or "resulted" respectively
   d. Absence of high probability of end-organ damage due to infection by displaying "–" under Severe Sepsis column
4. The Health Care Provider then selects the patient to further evaluate the reasons for Systemic Inflammatory Response Syndrome, presence of infection and presence of end organ damage due to infection by initiating the screening process.
5. Application calculates based on the user's input and validation of the information presented via the user interface to determine the presence of Systemic Inflammatory Response Syndrome, Infection and end organ damage due to infection. In this case the user determines that there is no infection present due to the absence of surrogate markers of infection. They select a reason for Systemic Inflammatory Response Syndrome that is not related to infection.
6. The dashboard screen now presents to the Health Care Provider the following information:
   a. Presence of Non-infectious cause of Systemic Inflammatory Response Syndrome by displaying "Non-Infectious Systemic Inflammatory Response Syndrome" under Systemic Inflammatory Response Syndrome column
   b. Absence of infection being the cause of Systemic Inflammatory Response Syndrome by displaying "Absent" under Sepsis column
   c. If the lab test has been sent it will display "sent" or "resulted" depending on if the lab test is available for review (resulted) or is still under processing (sent). It will further determine if the lab value is "normal" or "abnormal" and will display the same under column "Biomarker".
   d. Absence of end-organ damage caused by infection by displaying "–" under the Severe Sepsis column
7. The Health Care Provider by selecting the reason for "Non-Infectious Systemic Inflammatory Response Syndrome" via this process modifies the parameters of that discrete patient in order that their Systemic Inflammatory Response Syndrome alert will not trigger for the same reasons that triggered the initial alert. By this manner future false positives are avoided.

Usage Scenario 6: Existing patient updated in system and Application calculates a low probability of sepsis because the patient does not have sepsis (true negative).
1. Health Care Provider starts Application on device.
2. Health care provider reviews list of existing patients they have previously assigned themselves
3. The initial acuity dashboard screen presents the following comparative information for the Health Care Provider to consider, where the comparison is being made relative to other patients on that user's list of patients while calculating probability for that individual patient:
   a. Presence of low probability Systemic Inflammatory Response Syndrome by displaying "Absent" under Systemic Inflammatory Response Syndrome column
   b. Absence of surrogate markers of infection by displaying "–" under Sepsis column
   c. Indicating that biomarker labs are not required by displaying "–" in the "Biomarker" column
   d. Presence of low probability of end-organ damage due to infection by displaying "–" under Severe Sepsis column
4. In this scenario, the Health Care Provider will not further screen the patient and will not require allocation of time or other resources for evaluating the patient The foregoing description has been presented for purposes of illustration and description of preferred embodiments. This description is not intended to limit associated concepts to the various systems, apparatus, structures, and methods specifically described herein. For example, systems and methods described in the context of a patient (potentially) with sepsis, may be applicable to other medical conditions or patients with different and further symptoms (or collections of patient data). As well, systems and components described in the context of the treatment, management or diagnosis of sepsis, may be applicable and beneficial to other medical or patient-physician relationships The embodiments described and illustrated herein are further intended to explain the best and preferred modes for practicing the system and methods, and to enable others skilled in the art to utilize same and other embodiments and with various modifications required by the particular applications or uses.

What is claimed is:

1. A computer-implemented method of screening a patient for a medical condition, said method comprising:
   receiving patient data relating to an identified patient in a computing system including a processor and memory coupled to the processor, wherein the memory stores programmable instructions executable by the processor;
   determining the presence of Systemic Inflammatory Response Syndrome;
   receiving clinical parameters in the computing system;
   determining the presence of a probability of end organ damage due to infection; and
   wherein each of said receiving includes receiving, on a graphical user interface, one or more user selections presented on the graphical user interface, and wherein each said determining includes executing programmable instructions based on received user selections.

2. The method of claim 1, wherein each of said determining includes executing programmable instructions stored in said memory, with said user selections as input, to output patient status indicating, in the negative or affirmative, the presence of Systemic Inflammatory Response Syndrome or the presence of a high probability of end organ damage due to infection.

3. The method of claim 2, wherein said executing programmable instructions includes comparing received user selections with stored screening criteria, including a first screening criteria and a second screening criteria, wherein the patient data is compared to the first screening criteria for indicating the presence of Systemic Inflammatory Response Syndrome, and wherein the clinical parameters are compared to the second criteria for determining the presence of a probability of end organ damage due to infection.

4. The method of claim 3, wherein said determining the presence or absence of a probability of end organ damage due to infection includes executing programmable instructions to indicate a False Positive SIRS patient status based on said user selections.

5. The method of claim 4, further comprising:
   presenting, as user selection options on said graphical user interface, a set of sources for said False Positive SIRS patient status; and
   upon receiving a user selection of one of said sources for said False Positive SIRS patient status, recording said user selection as patient data associated with said identified patient.

6. The method of claim 1, further comprising, upon determining a high probability of end organ damage due to infection as patient status output to said executing programmable instructions, determining the presence of end organ damage due to infection, including receiving, on a graphical user interface, one or more user selections and executing programmable instructions, with at least one of said user selections as input, to output a patient status indicating the presence of end organ damage due to infection.

7. The method of claim 6, wherein said determining a high probability of end organ damage due to infection is preceded by executing programmable instructions to present, as user selection options on the graphical user interface, a plurality of clinical parameters, and wherein said executing programmable instructions includes comparing user selections received on the graphical user interface with stored screening criteria, including a screening criteria for comparing to the clinical parameters for identifying patient status indicating the presence of end organ damage due to infection.

8. The method of claim 7, wherein said clinical parameters include clinical parameters in the group of clinical parameters consisting of: Systolic Blood Pressure; MAP; Oxygen Saturation; Increasing Oxygen requirement; Decreased urine output; New or Altered Mental Status; Platelets level; Serum Lactic Acid level; and DIC/Petechiae.

9. The method of claim 7, further comprising:
generating a graphical user interface displaying a group of patient identities and, for each patient identity, a patient screening status display for indicating a patient screening status output stored for and associated with the patient identity; and
repeating said receiving patient data and said determining steps for a plurality of patient data, thereby identifying a plurality of identified patients; and
wherein, after each said determining step, a patient screening status output is stored in the memory such that said generating said graphical user interface displaying a group of patient identities includes displaying each of said patient screening status output in a patient screening status display.

10. The method of claim 7, further comprising, upon identifying a patient status indicating the presence of end organ damage due to infection, communicating a notice via the computing system to a remote station, the computing system including at least one display device whereon said graphical user interfaces are generated and wherein the remote station is configured to receive said notice.

11. The method of claim 1, further comprising:
providing a hand-held computing device as part of said computing system, said device having input means, output means, the processor, and the memory coupled to the processor, wherein the memory stores the programmable instructions executable by the processor and generates an output for display including:
programmable instructions executable to identify the patient; and
programmable instructions executable to determine the presence of Systemic Inflammatory Response Syndrome based on receipt of at least two patient-identified parameters through said input means.

12. The method of claim 3, wherein said determining the presence of a probability of end organ damage due to infection includes presenting user queries, on the graphical user interface, including presenting a set of query responses as user response options, and upon receiving one or more user selected query responses, comparing received query responses with the second screening criteria for determining the presence of a probability of end organ damage.

13. The method of claim 1, further comprising identifying the patient; and
wherein at least some of the patient data is retrieved from a database of historical patient data.

14. The method of claim 1, wherein determining the presence of said Systemic Inflammatory Response Syndrome includes comparing, with the aid of a graphical user interface, the patient data, including patient related conditions, with a first screening criteria, wherein the patient related conditions include patient temperature; patient heart rate; patient respiratory rate; patient white blood cell count; and patient blood glucose.

15. The method of claim 1, further comprising:
generating an acuity dashboard and displaying the acuity dashboard on a graphical user interface, wherein the acuity dashboard presents patient status.

16. The method of claim 1, wherein said clinical parameters comprise suspension of infection, recent antibiotic administration, recent medical procedure, presence of indwelling signs or catheters, and positive blood cultures.

17. The method of claim 1, wherein said determining comprises:
comparing the patient data to a first screening criteria and determining the presence of Systemic Inflammatory Response Syndrome based on the comparing; and
comparing the clinical parameters to a second screening criteria and determining the presence of a probability of end organ damage due to infection based on the comparing.

18. The method of claim 17, further comprising registering a patient status indicating the presence or absence of Systemic Inflammatory Response Syndrome, and registering a patient status indicating the probability of end organ damage due to infection.

19. The method of claim 17, further comprising:
receiving additional clinical parameters in the computing system; and
comparing the additional clinical parameters to a third screening criteria and determining the presence or absence of end organ damage due to infection.

20. The method of claim 19, further comprising calculating an acuity score for the patient based on an acuity of illness of the patient.

21. The method of claim 20, further comprising:
generating an acuity dashboard; and
displaying the acuity dashboard on a graphical user interface, wherein the acuity dashboard presents a patient status.

22. The method of claim 21, further comprising triaging multiple patients, including the patient, based on an acuity score of each patient.

23. A method of screening a patient for end organ damage due to infection, said method comprising:
providing patient data relating to an identified patient into a computing system including a processor and memory coupled to the processor, wherein the memory stores programmable instructions executable by the processor;
comparing the patient data to a first screening criteria and determining the presence of Systemic Inflammatory Response Syndrome; and
providing clinical parameters in the computing system;
comparing the clinical parameters to a second screening criteria and determining the presence of a probability of end organ damage due to infection; and
wherein each of said providing includes inputting, on a graphical user interface, one or more affirmative user selections presented on the graphical user interface and said determining includes initiating execution of the programmable instructions based on the inputted user selections.

24. The method of claim 23, wherein said graphical user interface includes user-activated prompts for each of a set of patient-identified parameters, and wherein said determining Systemic Inflammatory Response Syndrome includes, upon observing said patient, activating at least two of said prompts to select at least two patient-identified parameters, thereby determining the presence of Systemic Inflammatory Response Syndrome.

25. The method of claim 23, wherein each of said determining includes initiating execution of programmable instructions stored in said memory, with said user selections as input, to output patient status indicating, in the negative or affirmative, the presence of Systemic Inflammatory Response Syndrome or the presence of a probability of end organ damage due to infection.

26. The method of claim 23, wherein inputting a clinical parameter is preceded by selecting, on the graphical user interface, a clinical parameter selected from the group consisting of: SBP<90 mmHg; SBP<40 mmHg for baseline; MAP<65 mmHg; Oxygen Saturation<92%; Increasing Oxygen requirement; Decreased urine output; New or Altered Mental Status; Platelets<100,000; Serum Lactic Acid>15 mEq/L; DIC/Petechiae; and None of the Above.

27. A computing system, the system comprising:
at least one processor;
at least one display;
memory coupled to the at least one processor, wherein the memory stores programmable instructions executable by the at least one processor to present a plurality of graphical user interfaces on the at least one display, including a first graphical user interface and a second graphical user interface, and programmable instructions executable to determine the presence of a medical condition based on user selected patient information received on the plurality of graphical user interfaces; and
wherein the first graphical user interface presents, as user selection options, patient related conditions, and wherein said programmable instructions are executable to compare user selected patient related conditions received on said first graphical user interface with a first screening criteria to indicate the presence of an inflammatory response; and
wherein the second graphical user interface presents, as user selection options, a plurality of clinical judgment-based parameters, and wherein said programmable instructions are executable to compare user selected clinical judgment-based parameters received on said second graphical user interface with a second screening criteria to indicate a probability of end organ damage due to infection; and
wherein said programmable instructions are further executable to generate said second graphical user interface upon the indication of the presence of Systemic Inflammatory Response Syndrome.

28. A computer-implemented method of screening a patient for a medical condition, said method comprising:
receiving patient data relating to an identified patient in a computing system including a processor and memory coupled to the processor, wherein the memory stores programmable instructions executable by the processor;
comparing the patient data to a first screening criteria and determining the presence or absence of Systemic Inflammatory Response Syndrome;
registering a patient status indicating the presence or absence of Systemic Inflammatory Response Syndrome;
if the presence of Systemic Inflammatory Response Syndrome is determined, then: receiving clinical parameters in the computing system; and comparing the clinical parameters to a second screening criteria and determining the presence of a probability of end organ damage due to infection; and registering a patient status indicating the presence of the probability of end organ damage due to infection; and
after the presence of the probability of end organ damage due to infection is determined, then: receiving additional clinical parameters in the computing system; comparing the additional clinical parameters to a third screening criteria and determining the presence or absence of end organ damage due to infection; and registering a patient status indicating the presence or absence of end organ damage due to infection;
wherein each of said receiving includes receiving, on a graphical user interface, one or more user selections presented on the graphical user interface, and wherein each said determining includes executing programmable instructions based on received user selections.

\* \* \* \* \*